(12) United States Patent
Vadala, Jr. et al.

(10) Patent No.: US 9,433,716 B2
(45) Date of Patent: Sep. 6, 2016

(54) CONTROLLER AND POWER SOURCE FOR IMPLANTABLE BLOOD PUMP

(71) Applicant: HeartWare, Inc., Miami Lakes, FL (US)

(72) Inventors: Charles Joseph Vadala, Jr., Boston, MA (US); Jeffrey A. LaRose, Sunrise, FL (US); John Rudser, Miami, FL (US); Michael Ashenuga, Roslindale, MA (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 14/843,529

(22) Filed: Sep. 2, 2015

(65) Prior Publication Data

US 2015/0367047 A1 Dec. 24, 2015

Related U.S. Application Data

(62) Division of application No. 14/133,905, filed on Dec. 19, 2013.

(60) Provisional application No. 61/749,038, filed on Jan. 4, 2013.

(51) Int. Cl.
 *A61M 1/12* (2006.01)
 *A61M 1/10* (2006.01)
 *G06F 1/32* (2006.01)

(52) U.S. Cl.
 CPC ............. *A61M 1/12* (2013.01); *A61M 1/1053* (2013.01); *A61M 1/1086* (2013.01); *A61M 1/127* (2013.01); *A61M 2205/18* (2013.01); *A61M 2205/8206* (2013.01); *G06F 1/3212* (2013.01)

(58) Field of Classification Search
 CPC .. A61M 1/10; A61M 1/1001; A61M 1/1053; A61M 1/1086; A61M 1/12
 See application file for complete search history.

(56) References Cited

U.S. PATENT DOCUMENTS

| 6,123,726 A | 9/2000 | Mori et al. |
| 2003/0069465 A1 | 4/2003 | Benkowski et al. |
| 2010/0130809 A1 | 5/2010 | Morello |

(Continued)

OTHER PUBLICATIONS

Partial International Search Report for Application No. PCT/US2013/078209 dated Mar. 18, 2014.

(Continued)

*Primary Examiner* — Howie Matthews
(74) *Attorney, Agent, or Firm* — Lerner, David, Littenberg, Krumholz & Mentlik, LLP

(57) ABSTRACT

Methods and apparatus for controlling the operation of, and providing power for and to, implantable ventricular assist devices which include a brushless DC motor-driven blood pump, are disclosed. In one embodiment, a control system for driving an implantable pump is provided. The digital processor is responsive to data associated with the operation of the pump received at the data transfer port, and from the program data stored in memory, (i) to determine therefrom, the identity of the pump, (ii) to determine therefrom, electrical characteristics and features of the identified pump, and (iii) to adaptively generate and apply to the data port, control signals for driving the identified pump. Latch mechanisms, an elongated flexible electrical cable with a strain relief segment, and a lower housing portion that is heavier than an upper housing portion, may also be provided with the control system.

7 Claims, 10 Drawing Sheets

(56) References Cited

U.S. PATENT DOCUMENTS

2010/0241223 A1 9/2010 Lee et al.
2011/0218384 A1 9/2011 Bachman et al.
2012/0086402 A1 4/2012 Carder
2012/0157754 A1 6/2012 D'Ambrosio
2012/0157755 A1 6/2012 D'Ambrosio
2012/0226350 A1 9/2012 Rudser et al.

OTHER PUBLICATIONS

International Search Report and Written Opinion for Application No. PCT/US2013/078209 dated Aug. 7, 2014.

BLUE or WHITE
Situation Good

YELLOW
Alarm Condition

YELLOW
Alarm Condition

RED
Situation Requires
Immediate Attention

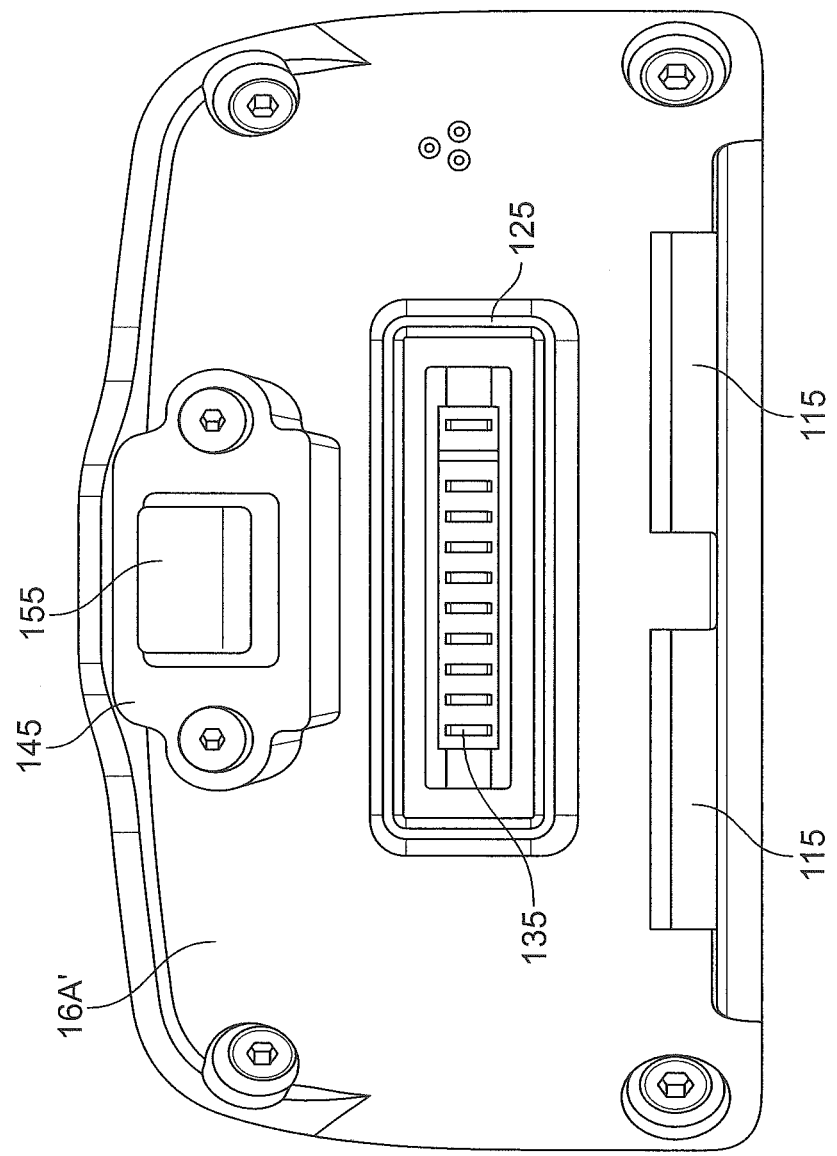

CONTROLLER AND POWER SOURCE FOR IMPLANTABLE BLOOD PUMP

CROSS-REFERENCE TO RELATED APPLICATIONS

The present application is a divisional of U.S. patent application Ser. No. 14/133,905, filed Dec. 19, 2013, which claims the benefit of the filing date of U.S. Provisional Patent Application No. 61/749,038 filed Jan. 4, 2013, the disclosures of which are both hereby incorporated by reference herein.

FIELD OF THE INVENTION

This invention relates to the field of implantable medical devices. In particular, this invention is drawn to controllers and power supplies for motor-driven implantable medical device applications.

APPLICATIONS INCORPORATED BY REFERENCE

U.S. Patent Publication No. 2012/0226350, titled "Controller and Power Source for Implantable Blood Pump" is hereby incorporated by reference herein. U.S. Patent Publication No. 2012/0086402, titled "Fault-Tolerant Power Supply" is hereby incorporated by reference herein.

BACKGROUND OF THE INVENTION

Implantable medical devices, such as ventricular assist devices, are being developed for long term treatment of chronic heart failure. Such devices require a pumping mechanism to move blood. Due to the nature of the application, the pumping mechanism must be highly reliable. Patient comfort is also a significant consideration.

Electrically powered pumping mechanisms typically rely on a motor such as a brushless DC motor. Brushless DC motors offer maintenance advantages in implant applications due to the lack of wear-prone brushes. Due to the lack of these electro and mechanical commutation components, commutation is generally provided electrically by drive electronics.

A prior art HeartWare Ventricular Assist System, manufactured by HeartWare Inc, Framingham Mass., is an example of an implantable ventricular assist device. At the core of the HeartWare Ventricular Assist System is a small implantable centrifugal blood pump called a HVAD® pump employing a brushless DC motor.

When implanted in a patient in a typical scenario, the pump draws blood from the left ventricle and propels that blood through an outflow graft connected to the patient's ascending aorta. The device is capable of generating up to 10 liters of blood flow per minute. With a displaced volume of only 50 cc, the HVAD pump is suitable for implantation in the pericardial space, directly adjacent to the heart. Implantation above the diaphragm leads to relatively short surgery time and quick recovery.

The HVAD pump has only one moving part, an impeller, which spins at a rate between 1800 and 4000 revolutions per minute. The impeller is suspended within the pump housing through a combination of passive magnets and hydrodynamic thrust bearings. This hydrodynamic suspension is achieved by a gentle incline on the upper surfaces of the impeller blades. When the impeller spins, blood flows across these inclined surfaces, creating a "cushion" between the impeller and the pump housing. There are no mechanical bearings or any points of contact between the impeller and the pump housing.

Device reliability is enhanced through the use of dual motor stators with independent drive circuitry, allowing a seamless transition between dual and single stator mode if required. The pump's inflow cannula is integrated with the device, and surgically implanted into the heart's ventricle. This proximity is expected to facilitate ease of implant and to help ensure optimal blood flow characteristics. The use of a wide-bladed impeller and clear flow paths through the system minimizes risk of pump-induced hemolysis (damage to blood cells) or thrombus (blood clotting).

Typically, while the pump is implanted in the patient, a controller and the drive electronics for the pump, and other control subsystems for the pump, including the power supply, are located outside the patient, for example, in a control/power supply module tethered by a transcutaneous electrical cable, to the implanted pump of the overall HeartWare Ventricular Assist System.

For the HeartWare Ventricular Assist System, an external (to the patient) controller includes the drive electronics for the pump (coupled directly to the windings of the motor) and provides drive and control signals to the pump. The controller also provides feedback and alarms to the patient regarding the operation of the device. Commutation control for the brushless DC motors is effected by the controller and the drive electronics, in a feedback manner. The controller provides a commutation control signal for a selected phase of the motor in accordance with a sampled back-emf voltage of that phase (sensed via the tether cable). The back-emf is sampled only while the corresponding selected phase drive voltage is substantially zero. The frequency of the brushless DC drive voltage is varied in accordance with the commutation control signal. In one form, the back-emf is normalized with respect to a commanded rotor angular velocity. A speed control generates a speed control signal corresponding to a difference between a commanded angular velocity and an angular velocity inferred from the frequency of the drive voltage.

A redundant power supply is provided by two batteries, or one battery and an AC adapter or DC adapter. The redundant power supply provides power for the controller, and particularly the drive electronics. When the battery is depleted (for example, after approximately 6 hours), the controller automatically switches to the standby power source, battery or adapter, and the depleted battery is replaced.

A "Patient Pack" assembly includes a carrying case that holds the controller and power source(s). The case can be adapted to be carried over the patient's shoulder or worn around the patient's waist.

While the prior art HeartWare Ventricular Assist System in the aggregate, performs the desired ventricular assist functions required for long term treatment of chronic heart failure, there is a need for improved subsystems and subassemblies which would provide enhanced blood flow results and improved patient-convenience features, easing the maintenance burden on the patient, thereby providing an improved quality of life.

BRIEF SUMMARY OF THE INVENTION

In one embodiment, a control system for driving an implantable blood pump includes a first housing including electronic components configured to drive the pump and a second housing including a battery. The first housing includes a first latch member extending from the first housing on a first side of the first housing and first and second recesses on a second side of the first housing. The second housing includes a third recess on a first side of the second housing and second and third latch members extending from the second housing on a second side of the second housing. When the first side of the first housing is aligned with the first side of the second housing, the first latch member aligns with the third recess, the second latch member aligns with the first recess, and the third latch member aligns with the second recess. The second and third latch members may each include bottom connected to the second housing and a top curving away from the first side of the second housing.

In another embodiment of the invention, a control system for driving an implantable blood pump includes an internal battery, an external battery, and a processor configured to perform an estimation of a remaining run time of the internal and external batteries. The estimation includes determining a remaining capacity of the internal battery, determining a remaining capacity of the external battery, determining a consumption rate of the internal battery, and determining a consumption rate of the external battery. Determining the remaining capacity of the external battery includes determining a value of the remaining capacity of the internal battery and modifying the value of the remaining capacity of the internal battery to account for a loss in efficiency when the external battery charges the internal battery.

In another embodiment of the invention, a control system for driving an implantable blood pump includes a first housing including electronic components configured to drive the pump, speakers, and a vibrating mechanism. The vibrating mechanism vibrates during a first interval following the detection of an alarm condition and the speakers sound an audible alarm during a second interval following the detection of the alarm condition. The first interval precedes the second interval, and the speakers are silent during the first interval.

BRIEF DESCRIPTION OF THE DRAWINGS

A more complete appreciation of the present invention and many of the attendant advantages thereof will be better understood by reference to the following detailed description when considered in connection with the accompanying drawings, wherein:

FIGS. 6A-E illustrate multiple views of an alternate embodiment of top and bottom housings of a control system.

DETAILED DESCRIPTION

Figure 1:
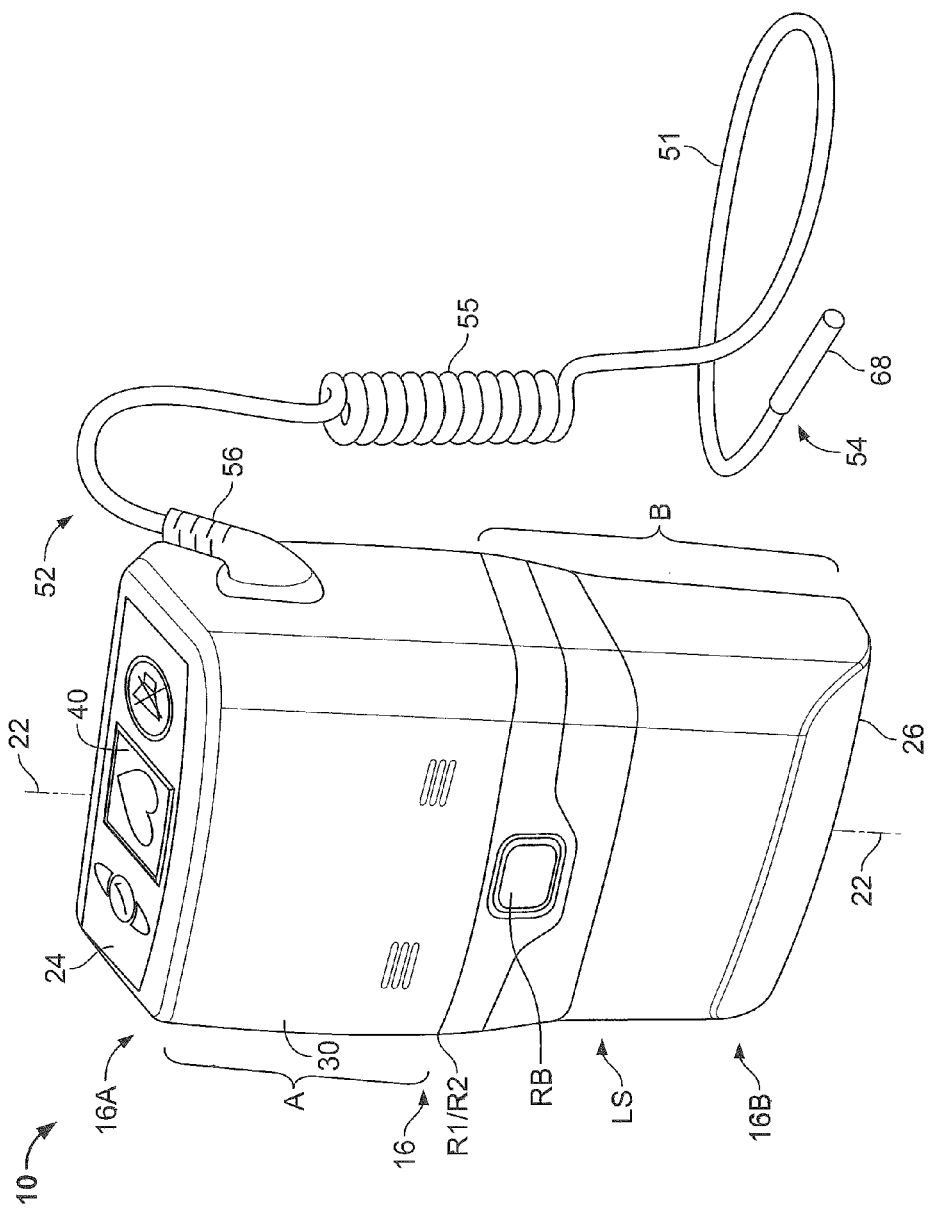
FIG. 1 is front-top-side view of a control system and connecting cable of the disclosure.

A control system 10 for controlling the operation of, and providing power for and to, implantable ventricular assist devices which include a pump employing a brushless DC motor-driven blood pump, is shown in FIGS. 1-4. The control system 10 is shown in diagrammatic form in FIG. 5, together with an exemplary pump 12.

As shown in FIGS. 1-5, the control system 10 includes a housing 16 disposed about an interior region 20. Housing 16 extends along a housing axis 22 between a top end 16A and a bottom end 16B. At the top end 16A, a top panel 24 having a substantially planar outer surface, extends transverse to the housing axis 22. At the bottom end 16B, a bottom panel 26 having a substantially planar outer surface, extends transverse to the housing axis 22. Lateral surfaces LS of housing 16 extend between the circumferential outer boundary of top panel 24 and the circumferential outer boundary of bottom panel 26. In the aggregate, the lateral surfaces of housing 16 form a tube-like structure extending along axis 22, with the end panels 24 and 26 forming closures to the tube, or tube-like, structure, enclosing the interior region 20.

The tube-like structure includes a first, or outer, portion 30 (referred to herein as "LS outer portion 30") opposite to a second, or inner, portion 32 (referred to herein as "LS inner portion 32"). Opposing uppermost portions of the outermost surfaces of LS outer portion 30 and LS inner portion 32 are substantially planar as well as substantially parallel, although as illustrated particularly in FIGS. 1-4, those portions are not precisely parallel. Different shapes and relationships may be employed in other embodiments.

A first display device 40 is disposed on the outer surface of top panel 24. A second display device 42 is disposed on the outer surface of the LS inner portion 32. The second display device 42 is optional and may be omitted from the control system 10. The housing 16 also includes on a lateral surface, a power port 46 and a data port 48 disposed within an input/output (I/O) connector assembly 49. An input device 50 is disposed on the outer surface of LS outer portion 30.

An elongated flexible electrical cable 51 extends from a controller end 52 to a pump end 54. The cable 51 further includes a flexible, helical-shaped strain relief segment 55 (shown in FIGS. 1-3) between the cable ends 52 and 54. A controller-end connector assembly 56 is disposed at the controller end 52, and a pump end connector assembly 60 is disposed at the pump end 54 of cable 51. The connector assembly 56 includes connector portions 46' and 48' adapted to mate with the power port 46 and the data port 48, respectively, of the I/O connector assembly 49.

The pump end connector assembly 60 similarly includes connector portions 62' and 64' adapted to mate with a pump power port 62 and pump data port 64 of a pump I/O connector assembly 68.

The controller-end connector assembly 56 is adapted to mate with an I/O connector assembly 49 on the housing 16, and the pump-end connector assembly 60 is adapted to mate with the pump connector assembly 68 on the pump 12.

When the controller-end connector assembly 56 is connected to the I/O connector assembly 49 of the controller 10, and the pump end connector assembly 60 is connected to the pump I/O connector assembly 68 of the pump 12, pump drive signals can pass between the power output port 46 and the pump power port 62. Data can pass between the data transfer port 48 and the pump data port 64, making available to data processor 32, the real-time impedances of the windings of the motor of pump 12.

In the illustrated embodiment, the housing is split into two opposed cup-like components: cup-like upper housing portion A having a circumferential rim R1, and cup-like lower housing portion B having a circumferential rim R2. Rim R1 of the upper housing portion A is adapted to interfit with and reversibly couple to the rim R2 of the lower housing portion B. A latch assembly enables the quick release of housing portion A from or to lower housing portion B, in response to depression of a release button RB disposed on the LS outer portion 30 of upper housing portion A (and an associated latch assembly. not shown). Rim R1 and rim R2 are shown in FIG. 1 by the reference symbol "R1/R2", and in FIG. 5, rim R1 and rim R2 are depicted as adjacent dashed lines extending across housing 16.

Figure 5:
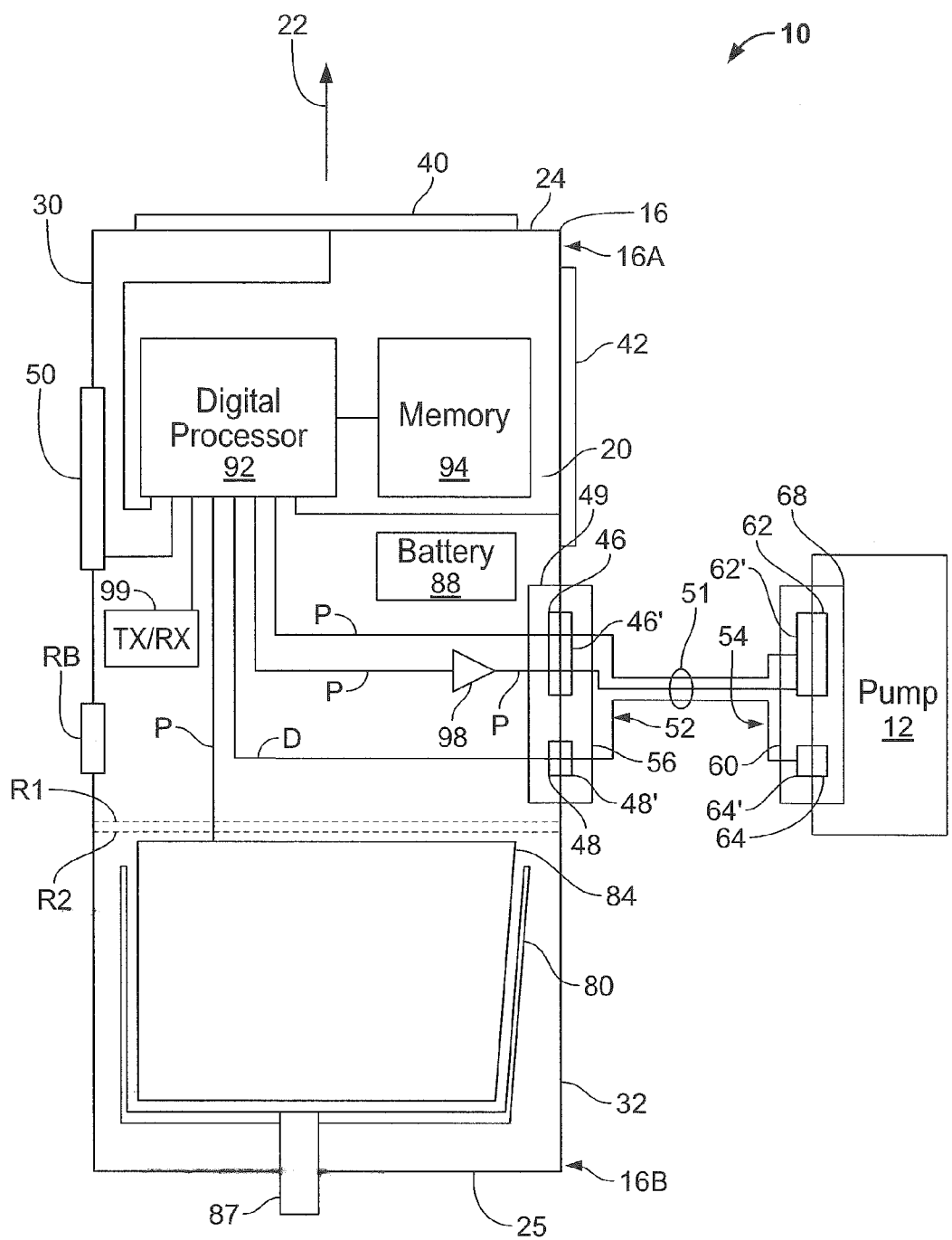
FIG. 5 is a diagrammatic representation of the control system and connecting cable of FIG. 1. together with an exemplary pump.

In the illustrated embodiment, the cup-like housing portion B provides electrical power for the operation of control system 10. As shown in FIG. 5, housing portion B includes in its interior, a power supply support structure 80. The support structure 80 has a cup-like form adapted to receive a battery 84 in its interior region. In some forms of the control system 10, the battery 84 is affixed to housing portion B and the portion B/battery module is replaceable as a unit. In other forms, the battery 84 is removably located in housing portion B, and is user-replaceable within housing portion B. In the illustrated form of FIG. 5, the interior of the power supply support structure 80 is geometrically keyed to the shape of the battery 84, to aid a user in replacing the battery in a fail-safe manner. In that structure, both the support structure 80 and the battery 84 are shown with geometric shape keying so that the battery 84 can only be inserted in support structure 80 in a single, proper manner. A secondary, or back-up, battery 88 is disposed within the interior of upper housing portion A, and is coupled to the various elements in control system 10, to provide back-up power to control system 10 in the event of catastrophic failure of battery 84 or during routine replacement of battery 84 with a charged or fresh unit.

As shown in FIG. 5 of the illustrated embodiment, the support structure 80 also includes power jack 87 so that the control system 10 can be powered by an external power source.

In the illustrated embodiment, the cup-like housing portion A houses the components which provide functional operation of control system 10, as it relates to the driving of an implanted pump 12. The housing portion A houses a digital signal processor 92 and an associated memory 94, a pump drive network 98, and, as noted above the secondary battery 88, as well as cabling which interconnects the various elements in the control system 10.

An electrical power conductor assembly P is disposed within interior region 20. That electrical power conductor assembly P is associated with the power supply support structure 80, and couples electrical power from a power supply (whether it be from a battery 84 disposed in support structure 80, from an external source by way of power jack 87 or from secondary battery 88), and provides electrical power to all elements in the control system 10. In addition, the electrical power conductor assembly P provides a power drive signal line from the digital processor 92, by way of a power amplifier 98, to the electrical power output port 46, where that power drive signal can be coupled via cable 51 to the motor (not shown) of pump 12.

A data conductor assembly D also is disposed within interior region 20. The data conductor assembly D provides analog "data" representative of the current state of the motor of pump 12, received via cable 51 at data transfer port 48, to the digital processor 92. In one form, that analog "data" is provided as a direct line to the windings of the motor of pump 12, from which the digital processor determines the impedance as a function of time of the respective windings of the motor. In response to that "impedance" data, the digital processor determines the appropriate drive power signal to be applied by way of power port 46 and cable 51, to the motor.

The input device 50 in some forms, includes a keyboard, and in other forms includes a connector, and in still other forms, includes both. Through the input device 50, a user of, or administrator for, the control system 10 can activate or deactivate the system 10, or can add, modify or delete any information associated with the operation of the system 10, for example by modifying the information stored in memory 94.

The control system 10 is adapted for use by an ambulatory patient who has an implanted blood pump. Under control of system 10, the patient's pump performs as programmed. For convenience, the patient can wear the control system 10 in a holster-like support extending about his or her waist, with the housing axis 22 substantially vertical and the LS inner portion against the patient's body. With this configuration, the patient can conveniently view the display device 40 on top panel 24, without removing control system 10 from the holster. An administrator, for example, a physician or nurse, who might hold the system 10 after removing it from the patient's holster, can view either display device 40 or display device 42 on LS inner portion 32. In the illustrated form, display 42 is relatively large compared to display device 40, so that more complex information can be displayed to the administrator while relatively simple, albeit highly useful, information can be displayed to the patient.

The memory 94 stores program information, for example, for controlling the operation of one of a number of (same or different model) implantable blood pumps which might be connected to, and driven by, the system 10. The digital processor 92 is adapted to run and control the overall system 10 as well as a pump attached thereto via cable 51. Display 42 is driven by the processor 92 to selectively display information which is generally useful to an administrator of a pump 12, such as a nurse or physician. In embodiments with or without the second display 42, the control system 10 may additionally be connected to a monitor, for example at a hospital or other clinical setting, which may display the type of information displayed on second display 42 or include additional, further detailed information that would otherwise be difficult to display on the second display 42.

In operation, the control system 10, when deployed, is coupled by way of cable 51 to a pump 12. Pursuant to its supervisory program from the memory 94, the system 10 determines from a coupled pump 12, the identity of the pump, for example the manufacturer and model number, the serial number, and in some cases the identity of the patient associated with the pump. From that determined identity information, system 10 determines certain electrical characteristics and features of the identified pump, and in some cases related to the patient associated with the pump. System 10 then adaptively generates and applies by way of the power port 46, control signals (e.g. pump drive signals) for driving the identified pump 12. As noted above, in the illustrated embodiment, the system 10 effectively monitors in real time, the operation of the pump 12, based on the impedance of the windings of the pump's motor, and generates appropriate time-based pump drive signals for application to those windings, to achieve the performance defined by the pump's program (which may be customized to the patient) stored in memory 94.

In one form, system 10 is adapted to control operation of one of a number of pumps of the same model, and the program information stored in memory 94 defines the features and modes of operation of the identified pump. In some cases this information is customized on a patient-by-patient basis, for each of a number of prospective pumps. In another form, system 10 is adapted to control operation of all of a number of different types of pumps. Similar control information is provided for each such pump in memory 94. In some cases, the pumps to be controlled are relatively passive, and provide information back to the control system 10 in the form of signal lines coupled to the windings of the pump motor, so that impedances can be detected and drive signals generated accordingly. In other cases, the pumps to be controlled are active, and provide over data port 48, data representative of various conditions in the pump, for example, identified faults, or data representative of certain conditions, such as indications of the occurrence of bases for an imminent failure of the pump. Among the various determinations made, system 10 generates a signal representative of the time remaining of operation under battery power, for the specific battery then installed, taking into consideration of the current state of charge and expected load/current drawdown. That time-remaining signal is selectively displayed on one, or both, of display devices 40 and 42 in human-readable form. The time-remaining value is based in part on the drive program associated with the pump, so as to provide a highly accurate reading all of the time remaining. When the time-remaining value reaches a threshold or range indicative of danger to the patient, an alarm is generated, for example, an audible alarm, a vibratory alarm, and a light alarm, solid or flashing.

Figure 3A:
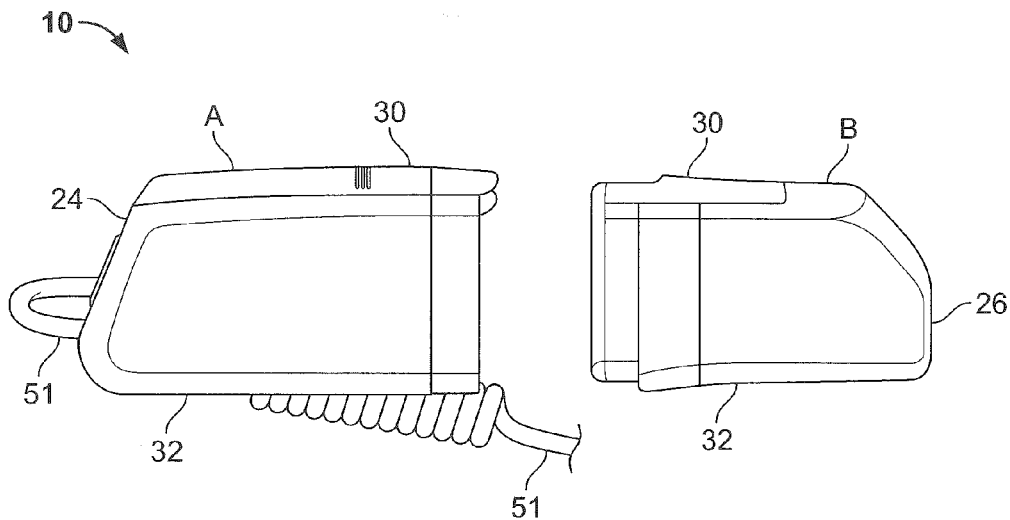
FIGS. 3A-B are side views of the control system and connecting cable of FIG. 1, showing a battery-containing portion detached from a processor-containing portion, and the battery-containing portion attached to the processor-containing portion, respectively.
Figure 3B:
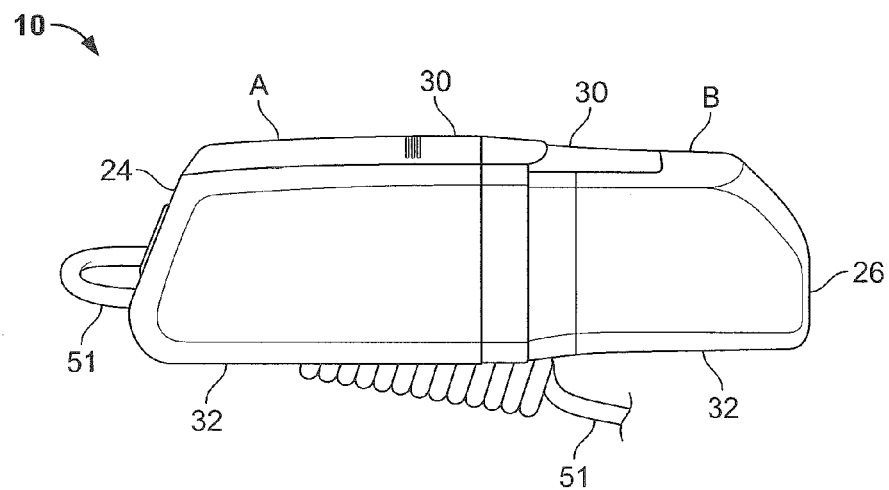

As noted above, the battery-containing lower cup-like portion B of housing 16 can be separated from the upper cup-like portion A (by depressing button RB), and a replacement lower cup-portion B with a fresh, fully charged battery, can replace the removed portion. A side view of the control system 10 is shown in FIG. 3A (with lower portion B of housing 16 attached to upper portion A of housing 16) and FIG. 3B (with lower portion B removed and displaced from upper portion A.

Also included within the housing 16, is a wireless transmitter/receiver TX/RX. A transmitter is coupled to the digital processor 92 and is adapted to selectively transmit and receive data. By way of example, the transmitted data may be representative of indicia of operation of a pump 12 under the control of system 10, to a main processor. The information can be selected to include data representative of broad aspects of the operation of the connected pump, such as pump activity, fault conditions, warning/alarm conditions and other data necessary for comprehensive logs for the pump. The received data, by way of example, may be program or control instructions, or modifications, for use in the control of system 10, and in turn, a pump attached thereto. In various forms, the control system 10 may include only a transmitter, or only a receiver, rather than the transmitter/receiver in the illustrated embodiment. In other embodiments, the data transfer may be accomplished via a wired line. This, for example, may be used when attaching the control system 10 to a hospital monitor to display highly detailed information stored on the control system 10.

Figure 2:
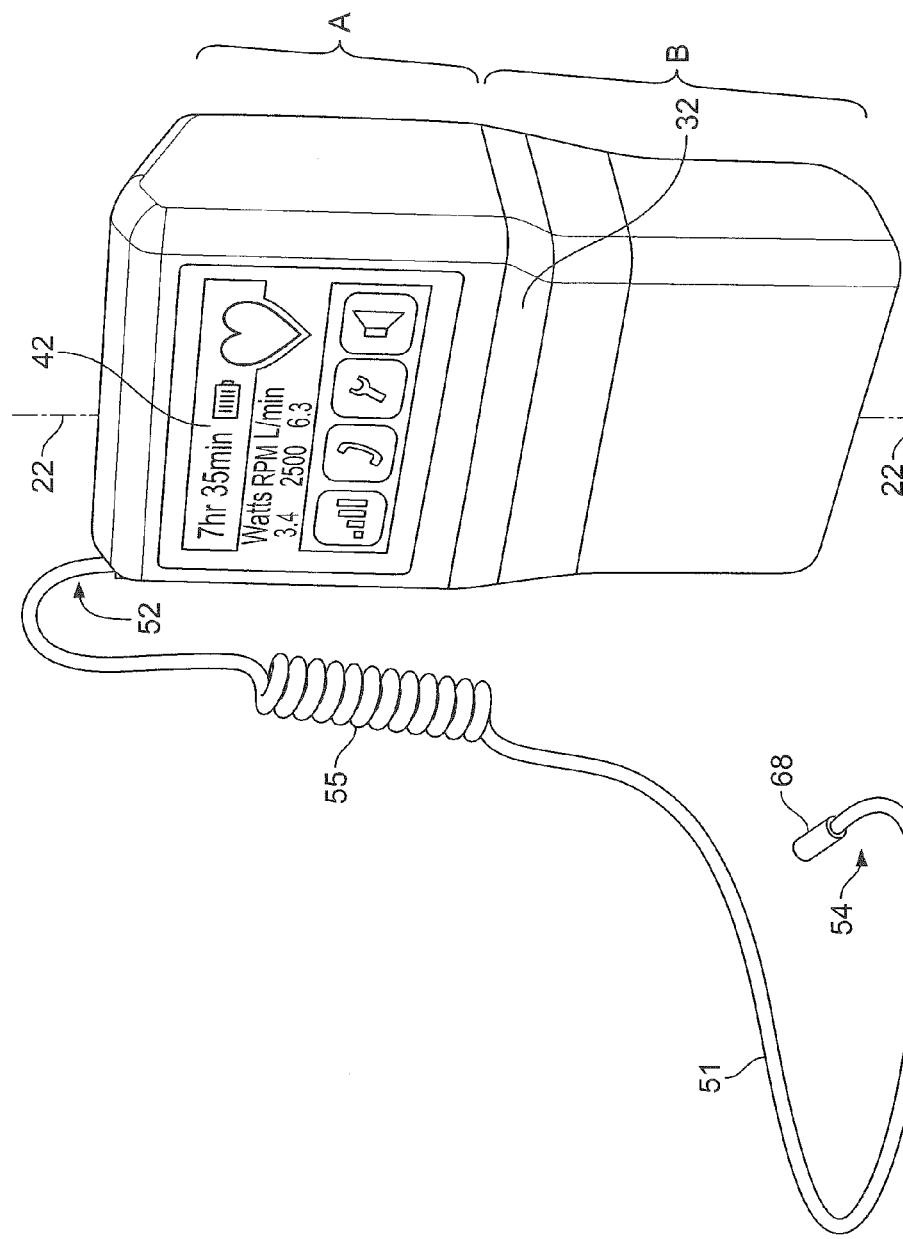
FIG. 2 is partially rear-side view of the control system and connecting cable of FIG. 1.

An exemplary set of information displayed on display device 42, is shown in FIG. 2. The data shown primarily in the form of icons or indicia. Indicia representative of length of time remaining for operation at the current state of battery (7 hours, 35 min.), battery life, characteristics of the pump attached to the system 10 (power being dissipated,=3.4 Watts, pump impeller rotational rate=22000 RPM, and pump output flow rate (6.3 Liters per minute), are all illustrated in FIG. 2. In addition, there is an icon overlying a membrane switch that can bring up data representative of signal strength relevant to the receiver RX, an icon in the shape of a telephone handset overlying a membrane switch that can initiate a telephone call, an icon in the shape of a wrench which overlying a membrane switch that can initiate a tool or setting screen, and an icon in the shape of loudspeaker overlying a membrane switch that can bring up an audio volume control screen. In addition, there is a condition (of control system 10) indicator, which in FIG. 2 is a heart-shaped icon that is indicative of "proper operation" of the pump of a patient connected to the system to. An alternative icon for the condition indicator is shown in FIG. 4D. The aforementioned data displayed on display device 42 is primarily of value to an administrator, such as a physician or nurse.

Figure 4A:
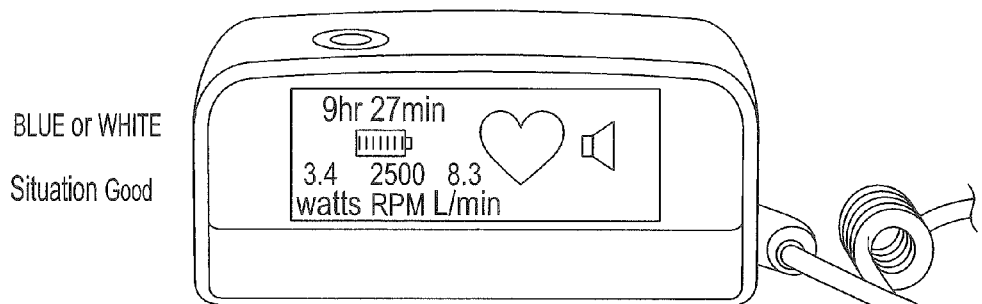
FIGS. 4A-D show top views of the top panel with a display device thereon, of the control system of FIG. 1.
Figure 4B:
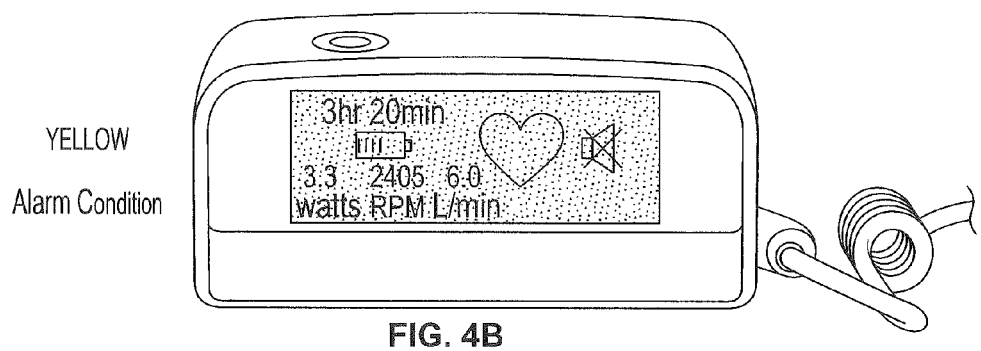
Figure 4C:
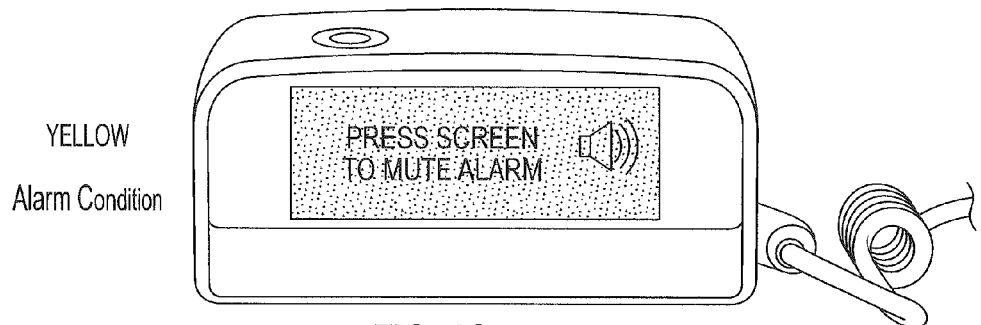
Figure 4D:
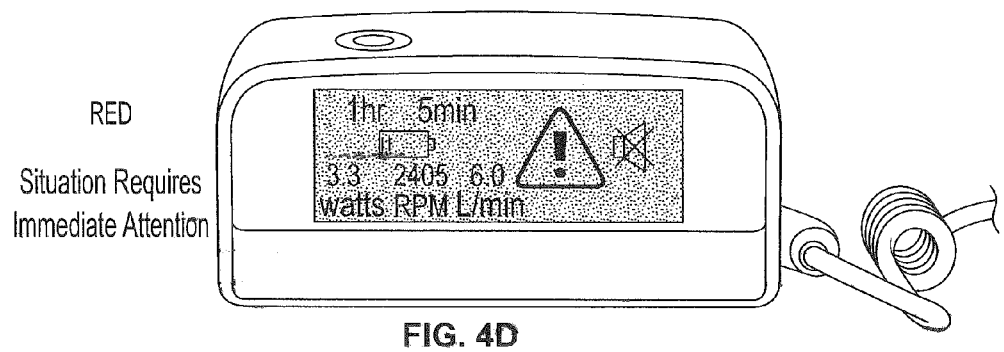

An exemplary set of information displayed on display device 40, is shown in FIGS. 4A-D. The data shown in FIGS. 4A-B and 40 is in the form of indicia representative of length of time remaining for operation at the current state of battery 84, battery life, and characteristics of the pump attached to the system 10 (power being dissipated, pump impeller rotational rate, pump output flow rate). There also is a loudspeaker-shaped icon indicative of auditory alarms being on or off (where an "X" overlays the loudspeaker-shaped icon when alarms are "muted temporarily"). As in the illustrated display device 42 in FIG. 2, there also is an icon that is indicative of "proper operation" of the pump of a patient connected to the system 10. In FIGS. 4A-B, that icon is heart-shaped, indicating "proper operation", or "situation good", of the pump of a patient connected to the system 10. In FIG. 4D, the condition indicator icon is in the form of the international traffic signal for "attention", a triangle with an exclamation point in its interior. The data in display device in FIG. 4A is representative of "all is well", and has a white or blue backlight. The data in display device in FIG. 4B is representative of "alert condition," and has a yellow backlight. When control system 10 is in its "alarm condition," the display 40 alternates with that shown in FIG. 4B and that shown in FIG. 4C, with the latter displaying "PRESS SCREEN TO MUTE ALARM," with a yellow backlight. The data in display device in FIG. 4D is representative of "Situation requires immediate attention," and has a red backlight.

The backlight values (blue/white, yellow, red) are qualitative indicators of great importance to the user/patient having his or her implanted blood pump under the control of the control system 10.

As described above, system 10 is capable of generating a signal representative of the time remaining of operation under battery power, for the specific battery then installed, taking into consideration of the current state of charge and expected load/current drawdown. The system 10 uses a runtime estimation algorithm to estimate the remaining runtime, or "Predicted Runtime," of both the external battery 84 and internal battery 88. The runtime estimation algorithm for both batteries 84, 88 may be periodically executed to determine the Predicted Runtime of each battery. Generally, Predicted Runtime is estimated as the ratio of the remaining battery capacity, or "Battery Capacity," to the rate of battery consumption, or "Consumption Rate." Stated otherwise, Predicted Runtime=Battery Capacity/Consumption Rate.

The internal battery 88 may include a battery management system (BMS) chip which may directly provide the remaining capacity of the internal battery 88. When the runtime estimation algorithm for the internal battery 88 is initiated, the value for Battery Capacity is equated to the remaining capacity provided by the BMS chip.

The external battery 84 may also include a BMS chip which may directly provide the remaining capacity of the external battery 84. However, for the external battery 84, the runtime estimation algorithm also takes into account the capacity of the external battery 84 to transfer charge to the internal battery 88, as well as efficiency losses and losses in the boost stage, when determining Battery Capacity. The capacity for the external battery 84 to transfer charge to the internal battery 88 is equated to the remaining capacity of the internal battery 88, provided by the BMS chip of the internal battery 88. This value may be modified with a Loss Coefficient to account for loss of capacity when charge is transferred from the external battery 84 to the internal battery 88. One such loss in efficiency may result from the boost circuit used in charging the batteries. For example, the algorithm may assume a 10% loss of capacity during transfer from the external battery 84 to the internal battery 88. If assuming a 10% loss of capacity, the capacity of the external battery 84 to transfer charge to the internal battery 88 would be calculated as the value of Battery Capacity for the internal battery 88 multiplied by the Loss Coefficient, in this case 1.1. Thus, the value for Battery Capacity of the external battery 84 is calculated as the difference between the remaining capacity of the external battery 84, as provided by the BMS chip of the external battery 84, and the capacity to transfer charge to the internal battery 88, as modified by a Loss Coefficient. Stated otherwise, External Battery Capacity=Loss Coefficient*Internal Battery Capacity.

The value determined for Consumption Rate at any given point may be determined by one of at least three different methods. The first method calculates an instantaneous consumption rate, determined as the product of average current and voltage of the battery. This first method may be used when certain conditions are met. For example, the first method may be used when (1) the internal battery 88 is not charging (i.e. it is either discharging or idle); (2) no AC power adapters are connected to the system 10; (3) the pump 12 is running; and (4) power is being provided to the system from the battery.

The second method for determining Consumption Rate is used when one of the conditions described with the first method is not satisfied. The second method entails using the most recently stored value calculated according to the first method. This second method, for example, prevents the Consumption Rate as being defined as 0 or another artificially small number when the pump has periodically stopped. If the first method was used when the pump had periodically stopped and there was an artificially low Consumption Rate, the value of Run Time would be calculated as an artificially high value. This artificially low Consumption Rate would not be expected to continue for the foreseeable future, as the pump would realistically start pumping again. Similar concerns arise for the other conditions described above. If the Consumption Rate is calculated according to the second method with both the internal battery 88 and external battery 84 connected, the value for Consumption Rate is used for the stored Consumption Rate of both batteries. If it is calculated only with the internal battery 88 connected, the value is used for the stored Consumption Rate of the internal battery 88 only.

If the system 10 is in an initialization phase, wherein no Consumption Rate has been stored according to the first method, and conditions for calculating the Consumption Rate according to the first method are not satisfied, a third method may be used. In the third method, a table of values is stored in memory to estimate the Consumption Rate based on the RPM of the pump 12 and a hematocrit setting previously entered by a user or administrator.

The Predicted Runtime calculated based on the determined values of Battery Capacity and Consumption Rate may then be digitally filtered. In a preferred embodiment, the filter used is a low pass infinite impulse response filter.

After filtering, the Predicted Runtime may then be discretized at different levels based on the magnitude of the Predicted Runtime. For example, if the Predicted Runtime is greater than 6 hours, the Predicted Runtime may be reported in increments of 30 minutes. As another example, if the Predicted Runtime is between 3.5 hours and 6 hours, the Predicted Runtime may be reported in increments of 15 minutes. Similarly, if the Predicted Runtime is between 1.5 hours and 3.5 hours, the Predicted Runtime may be reported in increments of 5 minutes. Further, if the Predicted Runtime is less than 1.5 hours, the Predicted Runtime may be reported in increments of 1 minute. For example, if the Predicted Runtime is calculated as 1.88 hours (1 hour and 52.8 minutes), it may be discretized such that the display reads a battery life of 1 hour and 50 minutes. The rationale is that, if the Predicted Runtime is comparatively long, it is less critical that the user know very precisely the amount of battery life remaining before requiring recharging or replacement of the battery. Contrariwise, if the Predicted Runtime is comparatively short, it is more critical that the user know very precisely the amount of battery life remaining before requiring recharging or replacing the battery. In one embodiment, the discretization algorithm always occurs downward, such that the discretized Predicted Runtime is always less than the calculated Predicted Runtime. The rationale for this embodiment is that it is better to provide the user with an underestimate of Predicted Runtime than an overestimate of Predicted Runtime.

As described above, an elongated flexible electrical cable 51 extends from a controller end 52 to a pump end 54 and includes a flexible, helical-shaped strain relief segment 55 (shown in FIGS. 1-3) between the cable ends 52 and 54. As one cable end 54 remains within the body when the pump 12 is implanted in the body while the other cable end 52 is outside the body connected to the control system 10, a portion of cable 51 extends through the patient's skin. The strain relief segment 55 is positioned outside the body. If the control system 10 is moved far enough away from the body, the relief segment 55 begins to unwind. By virtue of the relief segment 55 unwinding, the cable 51 does not significantly pull on the body site through which the cable 51 extends. If the cable 51 had no relief segment 55, tension on the cable 51 would directly translate to tension at the body site through which the cable 51 extends, or ultimately on the point of connection of the cable 51 to the pump 12. Avoiding such tension on the portion of the body through which the cable 51 extends also reduces irritation on the skin and promotes healing of the skin site through which the cable 51 extends. Additionally, the strain relief segment 55 may be calibrated such that if the control system 10 is dropped by the patient, the strain relief segment 55 will uncoil such that the control system 10 contacts the ground prior to the strain relief segment 55 fully uncoiling. This functions to reduce the likelihood that, if the control system 10 is dropped, the weight of the control system 10 will result in components of the pump 12 or cable 51 within the body causing internal bodily harm. In one example, the strain relief segment 55 uncoils or unwinds to a length of approximately 2 feet (0.610 meters) while the remainder of the cable 51 positioned outside the body is between approximately 18 inches (0.457 meters) and 2 feet (0.610 meters). In this embodiment, the total length of the cable 51, when the strain relief segment 55 is uncoiled or unwound, is between approximately 3.5 feet (1.067 meters) and 4 feet (1.219 meters). As the cable 51 usually exits the body near the lower abdomen area, the total length of the cable 51 outside of the body is enough for the control system 10 to reach the ground when the strain relief segment 55 is uncoiled.

In addition, as described above, cup-like lower housing portion B may adapted to receive a battery 84 in its interior region. Normally, the battery 84 is built into the housing B. The lower housing portion B, including its components, preferably is heavier than the upper housing portion A such that the center of gravity for the control system 10 is situated within the lower housing portion B. This may be accomplished by virtue of the weight of the battery 84 alone. Alternately, the lower housing portion B may be formed of heavier materials or may include additional material, such as weighted plates, to lower the center of gravity of the control system 10. Because the assembly of lower housing B and upper housing A has a low center of gravity, if the control system 10 is dropped, the lower housing portion B will be more likely to make initial contact with the ground. This may be beneficial in that the upper housing portion A, which houses the electronics to control the pump 12, is less likely to be damaged if the control system 10 is dropped and impacts the floor.

Still further, as described above, certain conditions of the control system 10, such as a low battery condition, may generate an alarm condition, for example by sounding an audible alarm or causing vibrations of the control system 10. In one embodiment, audible alarms are used in combination with vibratory alarms. In a further embodiment, the audible and vibratory alarms are staged in sequential phases. For example, as an operating condition is reached that causes the control system 10 to alert the user, a first stage vibratory alarm may be generated. Following a certain period of time, on the order of seconds, a second stage audible alarm may sound in addition to, or to replace, the vibratory alarm. The benefit of such a staged alarm configuration is that the vibratory alarm gives the patient a first notice of the alarm condition, upon which the user may act to temporarily mute upcoming audible alarms. This may be particularly beneficial if the user does not want to call attention to himself. Since it is generally imperative that a user become aware of an alarm condition in such a control system 10, it may be imprudent to set an alarm to solely a vibratory function, as a user may be more likely to fail to notice if a vibratory alarm is occurring. By allowing a staged alarm configuration, the user is given a first chance to privately notice and temporarily disable an alert notice. If the first vibratory alarm is overlooked, however, the control system 10 will produce a more noticeable audible alarm to increase the likelihood of the user becoming aware of the alarm condition.

As described above, an embodiment of the control system 10 includes an internal battery 88 and an external battery 84. An AC or DC power adapter may also be coupled to the control system to provide power. In one embodiment the external battery 84 may be removed from the control system 10 when the external battery 84 is low on charge and connected to a charging station to recharge the external battery 84. Alternatively, or in addition, the external battery 84, while connected to the control system 10, may be charged by the control system 10, while the control system 10 itself is being powered by a power adapter. This may be possible, for example, by a regulating circuit within the control system 10 that dictates the supply of power based on a set of hierarchy rules. In the hierarchy rules, if a power adapter is connected to the control system 10 while the external battery 84 is also connected, the control system directs the power to the external battery 84, the internal battery 88, and the pump 12. If the external battery 84 is not connected to the control system 10 but the power adapter is connected to the control system 10, the control system directs power to the internal battery 88 and the pump 12. If the power adapter is not connected to the control system 10, the control system 10 directs the external battery 84, if connected, to deliver power to the internal battery 88 and the pump 12. If neither the external battery 84 nor the power adapter is connected to the control system 10, only the internal battery 88 remains to power the control system 10 and pump 12.

An alternate embodiment of the control system housing 16' is illustrated in FIGS. 6A-E. In this embodiment, housing 16' includes upper housing 16A' and lower housing 16B'. Lower housing 16B' may accept a battery in a single configuration keyed to the shape of the lower housing 16B', or alternatively the lower housing 16B' may be integral with the battery, the battery and lower housing 16B' being provided as a unit. Many of the features of the housing 16' are similar or identical to features described in relation to housing 16 above. The illustrated embodiment of housing 16', however, includes an integrated latching mechanism to latch the battery/lower housing 16B' to the upper housing 16A'. As illustrated, battery/lower housing 16B' includes two latches 110 extending from an upper surface of the battery/lower housing 16B'. Each latch extends upwards and hooks back, away from the center of battery/lower housing 16B'. Near the center of the top of battery/lower housing 16B' is a recessed area 120, which may be generally rectangular. Within the recessed area 120 extend connecting pins 130, which allow electrical connection between the battery/lower housing 16B' and components of the upper housing 16A'. The battery/lower housing 16B may also include a plate 140 with recess 150 located on the opposite side of the latches 110. The plate 140 may be positioned lower than the top surface of the battery/lower housing 16B'.

Figure 6A:
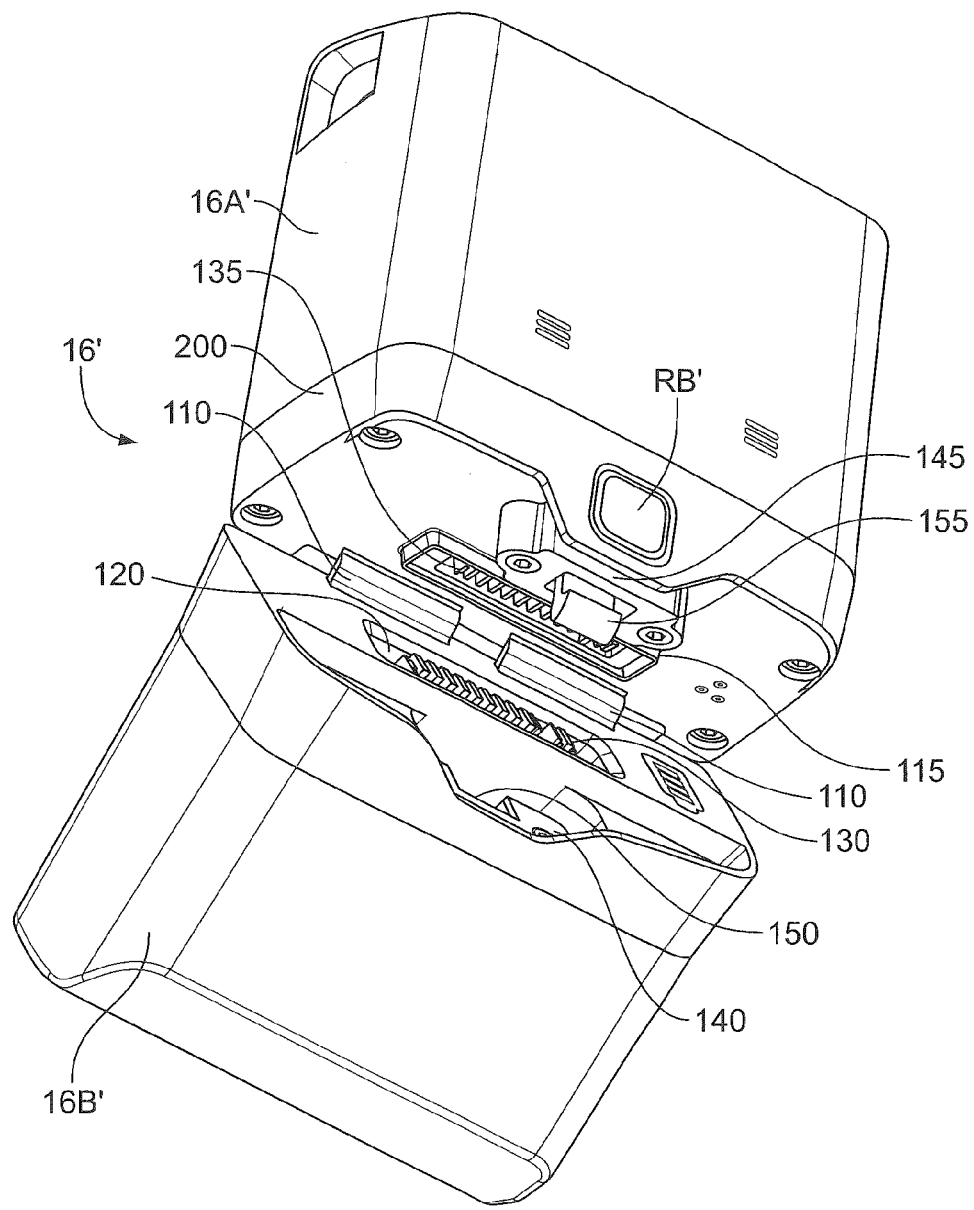
Figure 6B:
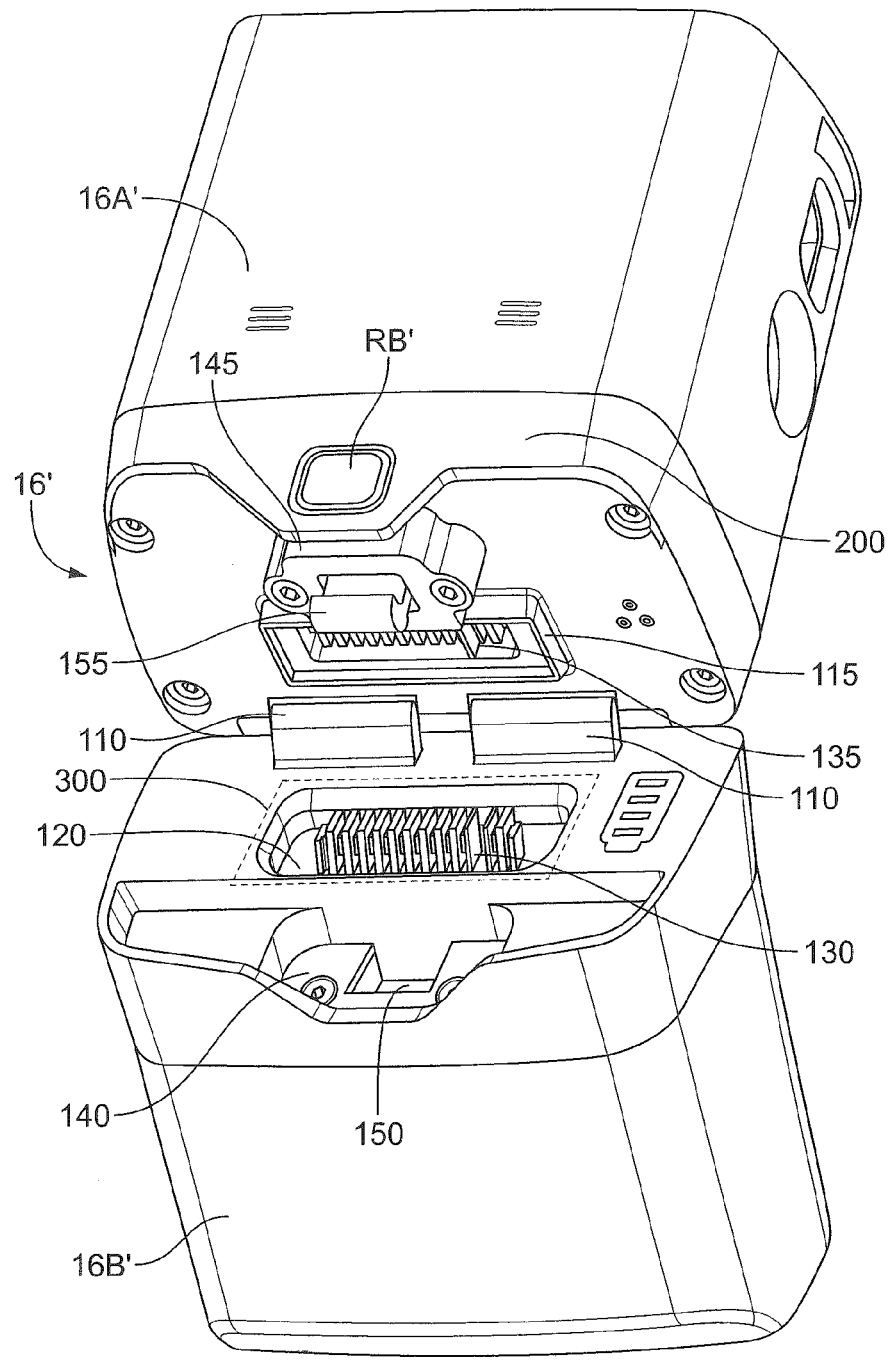
Figure 6C:
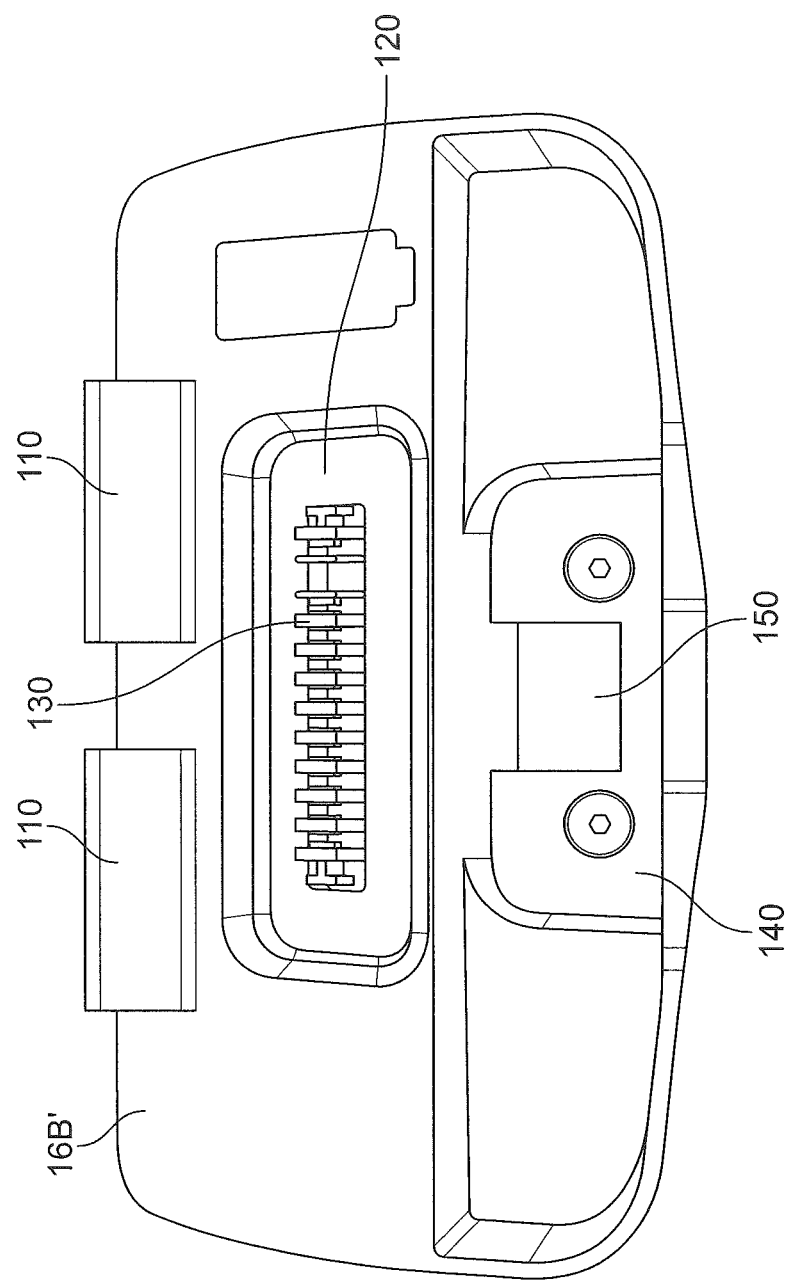
Figure 6E:
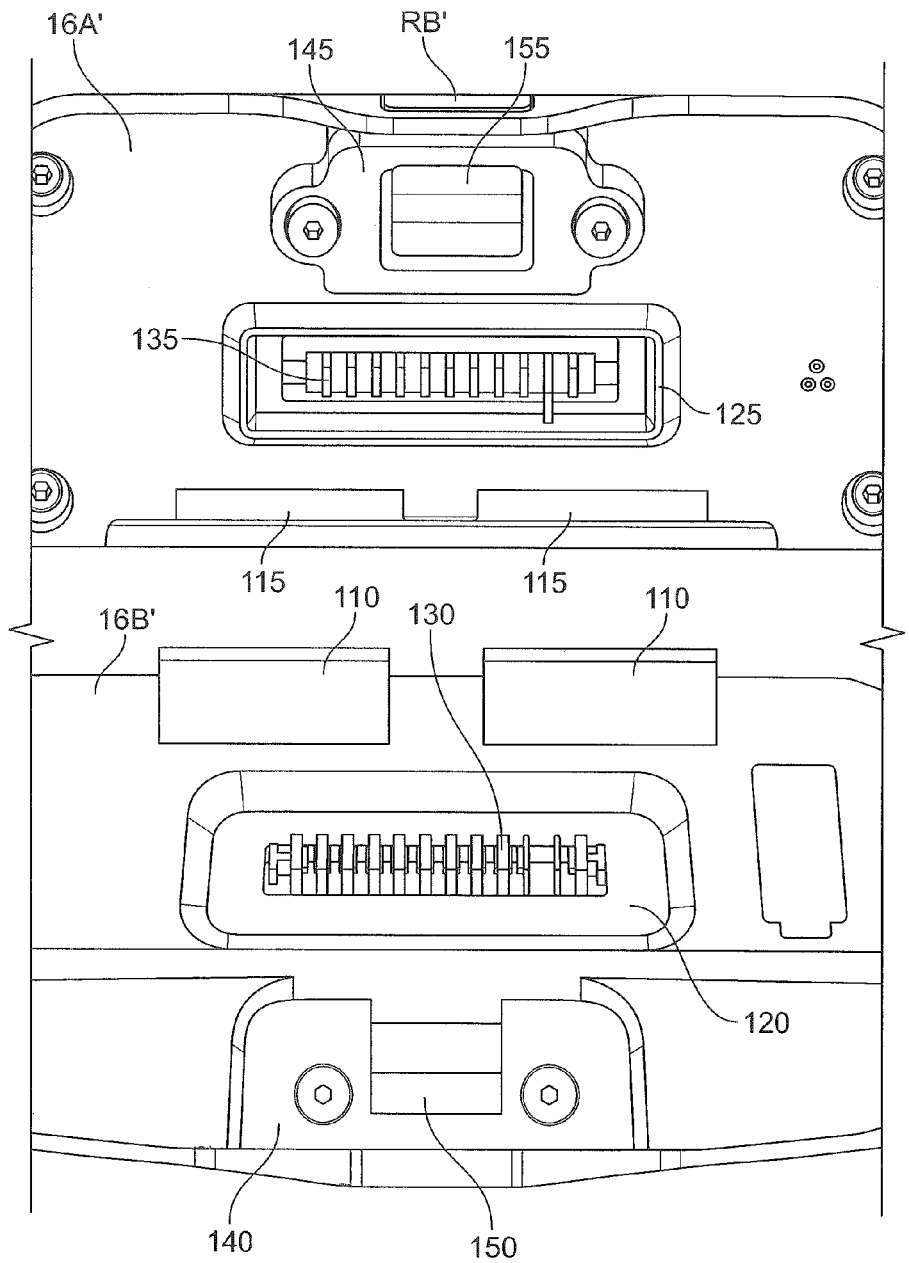

The bottom surface of upper housing 16A', the details of which are best illustrated in FIGS. 6D-E, includes features complementary to those of the battery/lower housing 16B'. For example, upper housing 16A' includes two generally rectangular recesses 115 configured to receive latches 110 of the battery/lower housing 16B'. Each latch 110 may be inserted into a respective recess 115, and as the upper housing 16A' is brought into contact with battery/lower housing 16B', the hooked shape of the latches 115 helps secure the housing 16' together.

The upper housing 16A' also may include a generally rectangular protrusion 125 near the center of the bottom of upper housing 16A', configured to fit within the recess 120 of battery/lower housing 16B'. Within a recessed area of the rectangular protrusion 125 of the upper housing 16A' are a set of connecting pins 135, which are configured to mate with the connecting pins 130 of the battery/lower housing 16B' to electrically connect the housing portions. After the latches 110 are inserted into the recesses 115 and the upper housing 16A' is rotated toward the battery/lower housing 16B', the rectangular protrusion 125 of the upper housing 16A' enters the rectangular recess 120 of the battery/lower housing 16B', after which the connecting pins 130, 135 mate with each other and electrically connect the housing.

The upper housing 16A' may further include a plate 145 and a latch 155 protruding through the plate, the plate 145 and latch 155 being positioned opposite the recesses 115.

When connecting the upper housing 16A' to the battery/lower housing 16B', after the latches 110 mate with the recesses 115, and after the connecting pins 130, 135 mate with each other, the upper housing 16A' continues rotation toward the battery/lower housing 16B'. As this motion continues, the latch 155 of upper housing 16A' enters the recess 150 of battery/lower housing 16B' as the plates 140, 145 make contact. This final latching action fully secures the upper housing 16A' to the battery/lower housing 16B'. As described above, the upper housing 16A' may include a release button RB'. If a user desires to disconnected the upper housing 16A' form the battery/lower housing 16B', he depresses the release button RB'. Once depressed, the latch 155 is unlocked from the recess 150, and the upper housing 16A' may be disconnected from the battery/lower housing 16B' in substantially the reverse order described above relating to connecting the upper housing 16A' with battery/lower housing 16B'.

Additionally, the bottom surface of upper housing 16A' may include a heat sink 200, for example comprising a material with good heat transfer properties. Such a heat sink 200 helps the control system 10 disperse heat generated during operation of the control system 10. A gasket 300 (illustrated in FIG. 6B), may also be provided between the upper housing 16A' and lower housing 16B' to help prevent water from entering the space between the upper housing 16A' and lower housing 16B'. Importantly, the gasket 300 helps exclude water from the connector pins 130, 135, through which electricity flows.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A control system for driving an implantable blood pump comprising:
    a first housing including electronic components configured to drive the pump;
    speakers; and
    a vibrating mechanism;
    wherein the vibrating mechanism vibrates during a first interval following the detection of an alarm condition,
    wherein the speakers sound an audible alarm during a second interval following the detection of the alarm condition,
    wherein the first interval precedes the second interval,
    wherein the speakers are silent during the first interval.

2. The control system of claim 1, wherein the alarm condition is a low battery condition.

3. The control system of claim 1, wherein the first interval is about 60 seconds or less.

4. The control system of claim 1, wherein, during the second interval, the vibrating mechanism does not vibrate.

5. The control system of claim 1, wherein, during the second interval, the vibrating mechanism does vibrate.

6. The control system of claim 1, further comprising a first display device coupled to first housing, wherein following the detection of the alarm condition, the first display device illuminates with one of a solid and flashing light alarm.

7. The control system of claim 6, further comprising a second display device coupled to the first housing, wherein following the detection of the alarm condition, the second display device illuminates with one of a solid and flashing light alarm.

* * * * *